United States Patent [19]

Otte et al.

[11] Patent Number: 4,695,660

[45] Date of Patent: Sep. 22, 1987

[54] METHOD OF PRODUCING CYCLOHEXYL COMPOUNDS

[75] Inventors: Werner Otte, Dorsten; Rudolf Nehring, Marl, both of Fed. Rep. of Germany

[73] Assignee: Hüls Aktiengesellschaft, Marl, Fed. Rep. of Germany

[21] Appl. No.: 888,711

[22] Filed: Jul. 24, 1986

[30] Foreign Application Priority Data

Oct. 19, 1985 [DE] Fed. Rep. of Germany ....... 3537228

[51] Int. Cl.$^4$ .................... C07C 29/132; C07C 29/136
[52] U.S. Cl. ...................................... 568/830; 568/831
[58] Field of Search ................................ 568/830, 831

[56] References Cited

U.S. PATENT DOCUMENTS 4,459,491 7/1984 Seemuth .............................. 568/831

FOREIGN PATENT DOCUMENTS 2220496 11/1974 France ................................. 568/830
0149950 12/1978 Japan ................................... 568/831

*Primary Examiner*—Werren B. Lone
*Attorney, Agent, or Firm*—Oblon, Fisher, Spivak, McClelland, & Maier

[57] ABSTRACT

A method of producing cyclohexyl compounds by catalytic hydrogenation of benzyl compounds, particularly acetophenone, whereby the benzyl compounds are hydrogenated in the presence of a catalyst comprising Ru and a support, with said benzyl compounds being in a slurry or a trickling liquid phase, at a hydrogen pressure of 200–350 bar, particularly 250–320 bar, and a temperatures of from 80° to about 160° C., particularly 100°–130° C., wherewith the catalyst contains Ru in the amount of, in particular, 0.1–1 wt. %.

6 Claims, No Drawings

METHOD OF PRODUCING CYCLOHEXYL COMPOUNDS

BACKGROUND OF THE INVENTION

1. Field of the Invention

The invention relates to a method for hydrogenating benzyl compounds, particularly acetophenone, in the presence of a Ru catalyst, to form the corresponding cyclohexyl compounds.

2. Discussion of the Background

The general object of the inventive method is to produce cyclohexyl compounds in a simple and economical procedure, with high purity and high yield.

1-Cyclohexyl-1-ethanol is of interest as a starting substance for producing vinylcyclohexane which is employed in polymer chemistry.

Hydrogenation of benzyl compounds to the corresponding saturated cyclohexyl compounds with the aid of Ru, Rh, and Pd catalysts is known, but the known methods are characterized by low yields, particularly due to the formation of cycloparaffins.

The principal means of eliminating these drawbacks has been the use of catalyst combinations, as described in USSR Pat. No. 733,710 (Ru+Cr, on alumina), USSR Pat. No. 405,323 (Rh+Ru, on alumina), USSR Pat. No. 448,703 (Ni+Cr), and *Tetrahedron Letters*, 17, 1663-1664 (1977) (Pd, Pd+Rh, Pd+Ru, on carbon); or by the addition of alkali, for example, as described in U.S. Pat. No. 3,366,695. The addition of acids is also known. These techniques do in fact lead to improved yields, but they require additional process steps.

According to *Zh. Prikl. Khim.*, 42(11), 2613-1614 (1969), Rh catalysts should be particularly suitable. Pd catalysts are relatively ineffective, particularly at higher pressures.

SUMMARY OF THE INVENTION

Accordingly, the object of the invention is to provide a method of producing cyclohexyl compounds by catalytic hydrogenation of benzyl compounds.

Surprisingly, it has been found in connection with the invention, that hydrogenation of acetophenone to 1-cyclohexyl-1-ethanol at relatively high pressures on commercially available Ru catalysts, with the Ru applied to inert supports such as, for example, alumina or silica, results in nearly quantitative yields.

The inventive method is characterized in that the benzyl compounds are hydrogenated in the presence of a catalyst comprising Ru and a support, in a slurry phase ("sump phase") or a trickling liquid phase, at a hydrogen pressure of 200-350 bar, and at temperatures from 80° C. to about 160° C.

DESCRIPTION OF THE PREFERRED EMBODIMENTS

The method of the present invention can be carried out in continuous or discontinuous fashion, with continuous operation being generally preferred. The apparatus needed for the inventive method is merely that of the state of the art, e.g., stirred autoclaves or reaction tubes. It is possible to carry out the inventive method in a slurry phase ("sump phase") or in a trickling liquid phase. In a batch operation, a slurry phase is ordinarily employed, using an autoclave and a powdered catalyst.

Particularly, the inventive method can be advantageously carried out in a continuous process. The process proceeds is customary manner, with catalysts in the form of particles (spheres, pellets, etc.) using trickling liquid phase techniques whereby the starting product flows as a liquid or as a liquid and vapor over the catalyst which is disposed in the reaction tube while the hydrogen is passed through the reaction tube in a cocurrent or countercurrent stream. It is advantageous to recycle excess hydrogen.

In general, the inventive method is carried out without the addition of a solvent. However, use of a solvent is not detrimental.

The invention method is carried out at a pressure greater than 100 bar, particularly above 200 or 250 bar, to approximately 320 bar; and at temperatures between 80° C. and 160° C., particularly between 100° C. and about 130° C. The LHSV is about 0.25.

The Ru catalyst employed in the inventive method is commercially available (e.g. from the firm Engelhard). The Ru in this catalyst is applied to inert supports, e.g. alumina or silica, in concentrations of 0.1 to 1% by weight, preferably 0.3-1%, and in particular 0.5%.

The particular advantages of the inventive method over known hydrogenation methods are that it can be carried out with smaller amounts of Ru than are needed under the state of the art (U.S. Pat. No. 3,366,695; *Zh. Prikl. Khim.*, 39(11), 2599-2601 (1966)), and that the use of noble metal mixtures (USSR Pat. Nos. 733,710 and 405,323; *Tetrahatron Letters*, 17, 1663-1664 (1967)), can be avoided. In addition, the cost of the noble metal is much less when using Ru than when using the previously preferred Rh (see *Chem. Lett.*, 5, 603-606 (1982); USSR Pat. No. 448,703; *Zh. Prikl. Khim.*, 2398-2400 (1969); ibid., 11, 2613-2614).

In addition, very good results can be obtained with noble metal concentrations on the order of or even less than 1/10 of customary concentrations. According to the invention, good results can be obtained with 2.5-5 g Ru metal per ton of acetophenone.

The inventive method, therefore, produces cyclohexyl compounds economically and in high yields.

Other features of the invention will become apparent in the course of the following descriptions of exemplary embodiments which are given for illustration of the invention and are not intended to be limiting thereof.

EXAMPLE 1

100 ml/hr acetophenone (c. 0.83 mol/hr) and 400 liter/hr (based on standard temperature and pressure, "S.T.P.") hydrogen (c. 18 mol) were passed through a 400 ml tubular reactor filled with a catalyst of 0.5 wt.% Ru on alumina (catalyst supplied by Engelhard), at 300 bar overall pressure and 110° C. The hydrogenation outlet stream had the following composition as determined by gas chromatography:

First runnings: 0.3%
Ethylcyclohexane: 1.7%
Intermediate runnings: 0.2%
Acetophenone: --
1-Cyclohexyl-1-ethanol: 96.4%
Tails: 1.4%

The acetophenone used had a purity of 96.7%.

After an operating time of 2200 hr, the run was interrupted. There was practically no loss of catalyst selectivity or activity.

EXAMPLE 2

The procedure of Example 1 was followed except that the feed used was a solution comprised of equal parts by weight of acetophenone and 1-cyclohexyl-1-ethanol. The hydrogenation outlet stream had the following composition:
First runnings: 0.5%
Ethylcyclohexane: 1.9%
Intermediate runnings: 0.3%
Acetophenone: --
1-Cyclohexyl-1-ethanol: 95.8%
Tails: 1.5%

The feed was comprised of acetophenone (48.4%), and 1-cyclohexyl-1-ethanol (48.2%), with the remainder being first runnings, intermediate runnings, and tails.

EXAMPLE 3

The procedure of Example 1 was followed, except that the temperature was reduced to 90° C. The hydrogenation outlet stream had the following composition:
First runnings: 0.1%
Ethylcyclohexane: 0.8%
Intermediate runnings: 0.5%
Acetophenone: 6.1%
1-Cyclohexyl-1-ethanol: 91.0%
Tails: 1.5%

The acetophenone used had a purity of 97.4%.

EXAMPLE 4

The procedure of Example 1 was followed except that the temperature was increased to 150° C. The hydrogenation outlet stream had the following composition:
first runnings: 1.2%
Ethylcyclohexane: 4.1%
Intermediate runnings: 0.3%
Acetophenone: --
1-Cyclohexyl-1-ethanol: 92.9%
Tails: 1.5%

The acetophenone used had a purity of 97.4%.

EXAMPLE 5

The procedure of Example 1 was followed, except that the pressure was reduced to 200 bar. The hydrogenation outlet stream had the following composition:
First runnings: 0.2%
Ethylcyclohexane: 1.2%
Intermediate runnings: 0.2%
Acetophenone: 0.9%
1-Cyclohexyl-1-ethanol: 96.1%
Tails: 1.4%

The acetophenone used had a purity of 97.4%.

COMPARATIVE EXAMPLE 1

The procedure of Example 1 was followed, except that a catalyst of 0.5 wt.% Pd on alumina (supplied by Engelhard) was used. The hydrogenation outlet stream had the following composition:
First runnings: 0.4%
Acetophenone: trace
Ethylcyclohexane: 65.2%
Intermediate runnings: 2.6%
1-Cyclohexyl-1-ethanol: 29.5%
Tails: 2.3%

COMPARITIVE EXAMPLE 2

The procedure of Example 1 was followed, except that a catalyst of 0.5 wt.% Pd on alumina (supplied by Engelhard) was used, the pressure was reduced to 15 bar, and the temperature was reduced to 90° C. The hydrogenation outlet stream had the following composition:
First runnings: 0.2%
Acetophenone: 0.8%
Ethylbenzene: 34.2%
Intermediate runnings: 2.0%
Methylbenzyl alcohol: 61.1%
Tails: 1.7%

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A method for producing 1-cyclohexyl-ethanol by catalytic hydrogenation of acetophone, comprising:
hydrogenating said acetophenone in the presence of a catalyst consisting essentially of Ru and a support, at a hydrogen pressure of about 200-350 bar and a temperature of from about 80°-160° C. and wherein said acetophenone is in a slurry or a tricking liquid phase.

2. The method of claim 1, wherein said catalyst contains 0.1-1 wt. % of Ru.

3. The method of claim 2, wherein said catalyst contains 0.5 wt.% Ru.

4. The method of claim 1, wherein said support is $Al_2O_3$.

5. The method of claim 1, wherein said hydrogenating step is carried out at a hydrogen pressure of from 250-320 bar.

6. The method of claim 1, wherein said hydrogenating step is carried out at temperatures of from about 100° C. to about 130° C.

* * * * *